United States Patent [19]

Griffis

[11] Patent Number: 4,993,272
[45] Date of Patent: Feb. 19, 1991

[54] AIR SAMPLER

[76] Inventor: Steven C. Griffis, 2929 Avenue D, Council Bluffs, Iowa 51501

[21] Appl. No.: 433,562

[22] Filed: Nov. 8, 1989

[51] Int. Cl.$^5$ .............................................. G01N 1/14
[52] U.S. Cl. ................................................. 73/863.83
[58] Field of Search ........... 73/863.21, 863.23, 863.31, 73/863.83, 864.34; 55/270; 40/553; D20/19/20

[56] References Cited

U.S. PATENT DOCUMENTS

| 4,080,832 | 3/1978 | Moody et al. | 73/863.23 |
| 4,235,098 | 11/1980 | Tisch | 73/863.23 |
| 4,616,513 | 10/1986 | Gibson et al. | 73/863.23 |
| 4,831,438 | 5/1989 | Bellman, Jr. et al. | 358/210 |

FOREIGN PATENT DOCUMENTS 3615111 11/1987 Fed. Rep. of Germany ... 73/864.34

Primary Examiner—Robert Raevis
Attorney, Agent, or Firm—Zarley, McKee, Thomte, Voorhees & Sease

[57] ABSTRACT

An air sampler is described which appears to be nothing more than a bulletin board or the like. The air sampler is contained within a housing and has a pair of air sampling cassettes positioned therein which sample the air surrounding the air sampler.

3 Claims, 3 Drawing Sheets

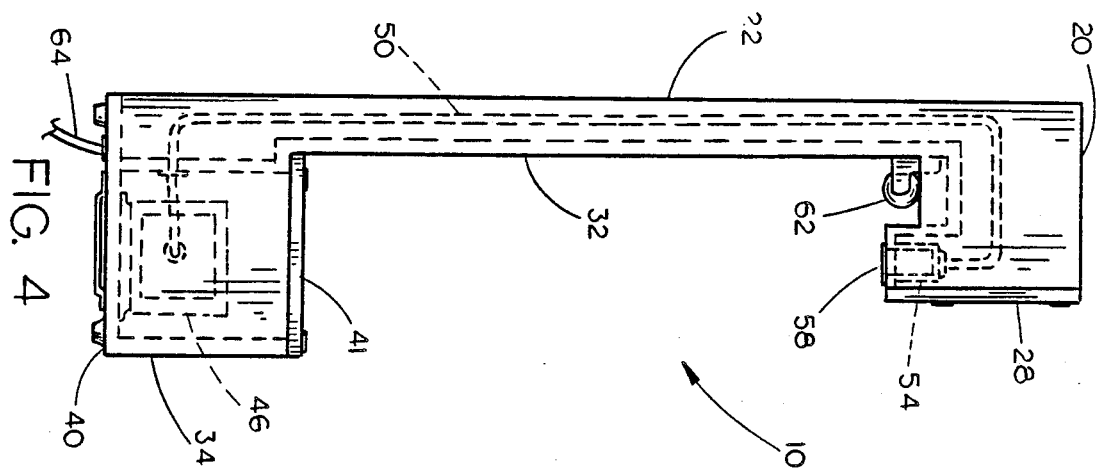
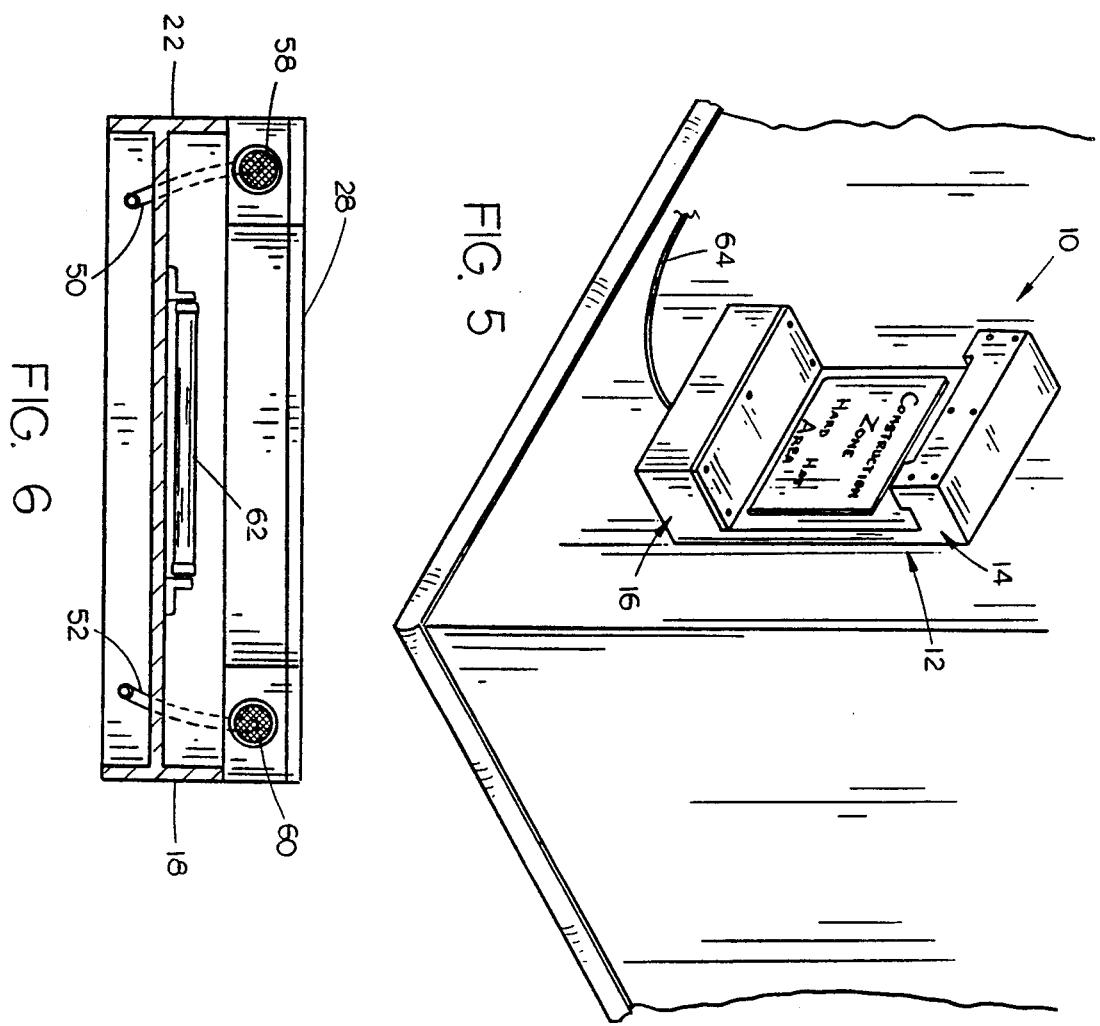

4,993,272

AIR SAMPLER

BACKGROUND OF THE INVENTION

Asbestos abatement actions are normally conducted within an enclosed confinement or containment area. The air within the enclosed contaminated space is required to be sampled and the same is accomplished by means of an air pump which draws air into a sampling cassette positioned in a cassette holder. It is also a requirement that the air outside the enclosed contaminated area be sampled.

In the past, the air outside the enclosed contaminated area was sampled in the same fashion as the air within the enclosed contaminated area, that is, an air pump connected to a sampling cassette. The customary way of sampling the air outside the work area poses many problems. In some cases, it has been found that janitorial crews may attempt to dust or otherwise clean the sampling cassette with the dusting procedure creating false readings in the cassette. Perhaps the biggest drawback is the fact that the presence of air samplers attracts the curious and alerts employees or the public that the air may be contaminated since it is apparently necessary to monitor or sample the air.

It is therefore a principal object of the invention to provide an air sampler which does not look like an air sampler.

A further object of the invention is to provide an air sampler which simply looks like a sign support and therefore does not readily indicate that air is being sampled.

Still another object of the invention is to provide an air sampler which is positioned in an aesthetically attractive housing including means for illuminating a sign on the housing and means for cooling the air pumps located within the housing.

Still another object of the invention is to provide an air sampler which is economical of manufacture, durable in use and refined in appearance.

These and other objects of the present invention will be apparent to those skilled in the art.

BRIEF DESCRIPTION OF THE DRAWINGS

FIG. 4 is a side elevational view of the air sampler;

FIG. 5 is a perspective view illustrating the air sampler mounted on the exterior of an enclosure wherein an asbestos abatement action is being conducted; and FIG. 6 is a sectional view as seen on line 6—6 of FIG. 2.

SUMMARY OF THE INVENTION

Figure 1:
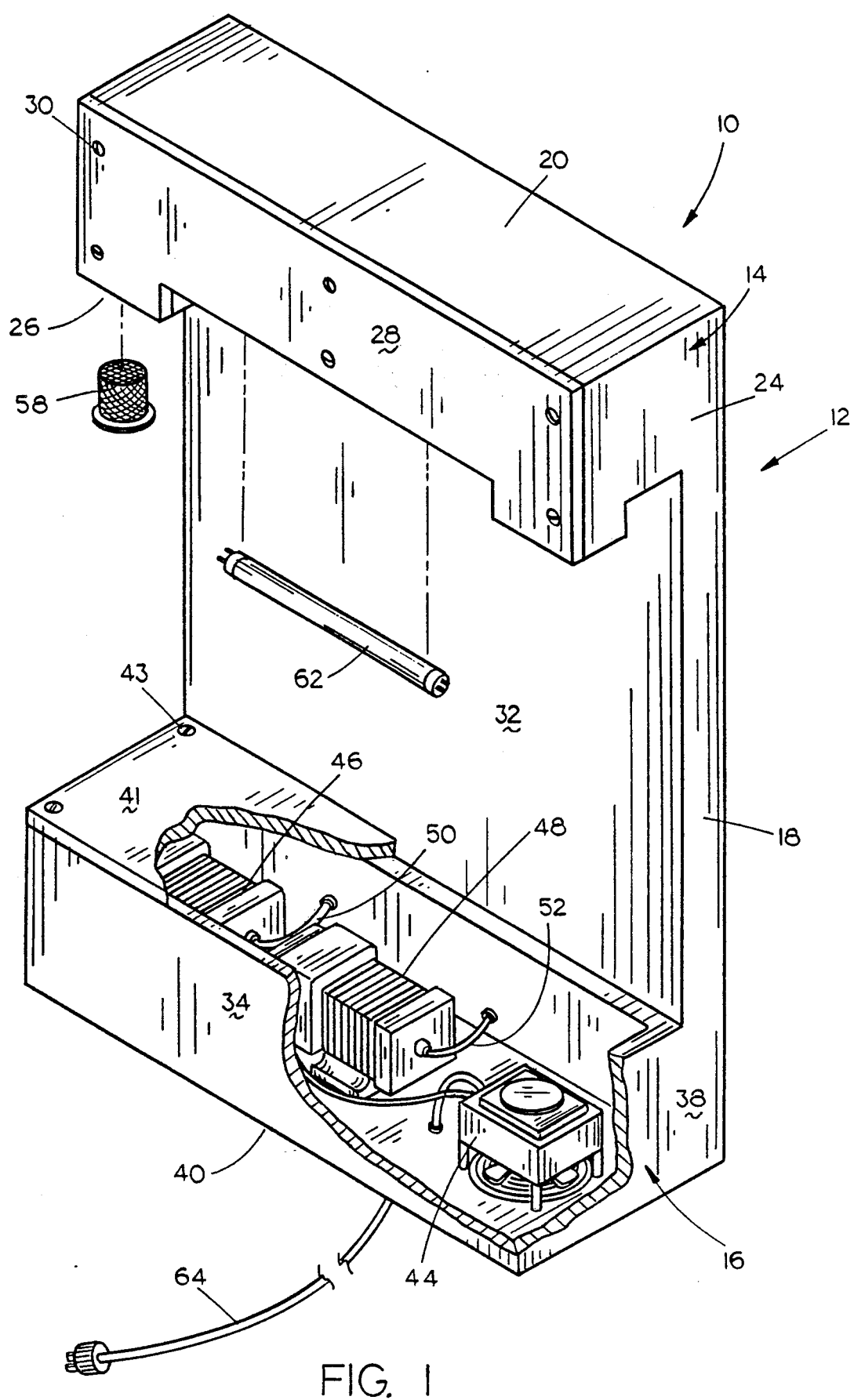
FIG. 1 is a perspective view of the air sampler of this invention with portions thereof broken away to more fully illustrate the invention.
Figure 2:
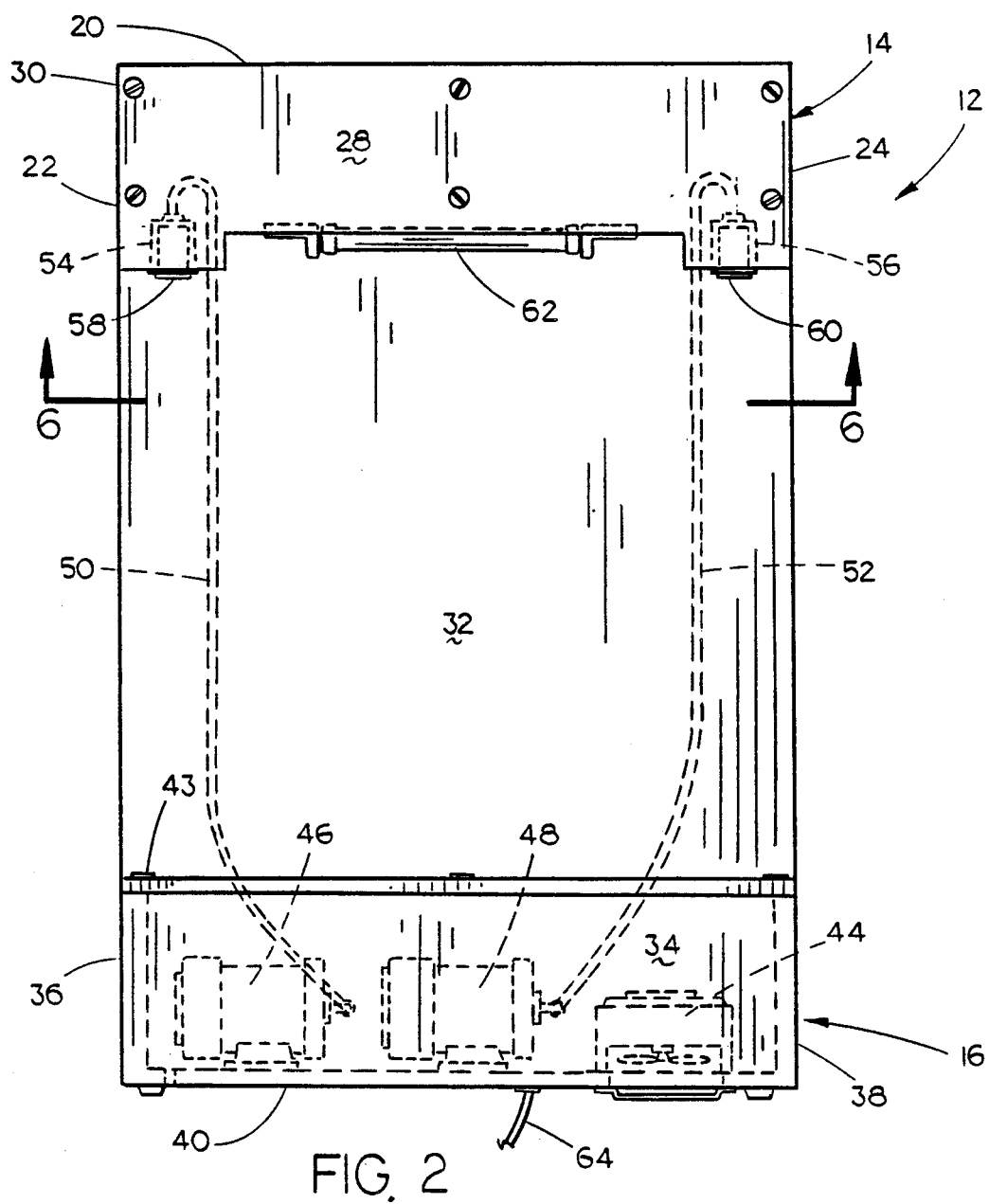
FIG. 2 is a front elevational view of the air sampler.
Figure 3:
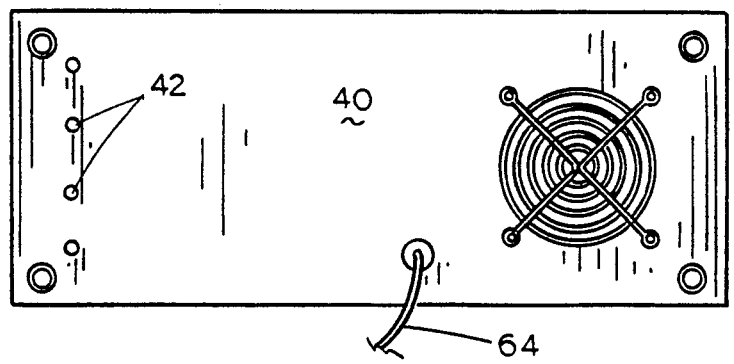
FIG. 3 is a bottom view of the air sampler.

The air sampler of this invention comprises upper and lower housing members joined by a connecting housing member. The back housing member serves as a sign support so that the apparatus appears to be a sign rather than an air sampling unit. A pair of recessed cassette holders are positioned in the upper housing member for supporting sampling cassettes therein in such a manner so that the cassettes are in communication with the air surrounding the sampler but are not readily visible. A pair of air pumps are located within the lower housing member and are operatively connected to the cassette holders so that air may be drawn into the sampling cassettes. A cooling fan is provided in the lower housing member for cooling the air pumps. A light is provided in the upper housing member for illuminating the sign positioned on the connecting housing member.

DESCRIPTION OF THE PREFERRED EMBODIMENT

The air sampler of this invention is referred to generally by the reference numeral 10 and comprises a housing 12 including upper housing member 14, lower housing member 16, and connecting housing member 18. For purposes of description, upper housing member 12 will be described as including a top portion 20, opposite sides 22 and 24, and bottom 26. The front portion of upper housing member 14 is selectively closed by means of a front cover 28 secured in place by screws 30.

Connecting housing member 18 includes a front portion 32 upon which is positioned a sign or the like warning employees and/or the public that construction work is in progress nearby.

Lower housing member 16 includes a front portion 34, opposite sides 36 and 38 and bottom 40. The upper end of lower housing member 16 is selectively closed by means of a cover 41 maintained in position by screws 43.

The bottom 40 of lower housing member 16 is provided with a plurality of vent openings or holes 42 and a cooling fan 44 which draws air into the lower housing member 16 through the vent openings 42 so that the air pumps 46 and 48 will be cooled. Hoses 50 and 52 extend from air pumps 46 and 48 upwardly through the interior of connecting housing member 18 and are operatively secured to cassette holders 54 and 56 respectively. The cassette holders 54 and 56 are recessed into the bottom 26 of upper housing member 14 and are adapted to have sampling cassettes 58 and 60 mounted therein respectively. By recessing the cassette holders 54 and 56 into the bottom of upper housing member 14, the cassettes 58 and 60 will be inconspicuous so that only the most inquisitive person would observe that sampling cassettes are located in the apparatus and that the air is being sampled. A fluorescent light 62 is also positioned at the underside of upper housing member 14 for illuminating the area 32. Power cord 64 extends from lower housing member 16 and is connected to a source of electrical power for supplying electrical power to the air pumps 46 and 48, for 44 and the light 62.

Thus, the air sampler of this invention may be mounted on a wall outside an area where asbestos abatement actions are being conducted so that the air may be sampled as required. By positioning the air sampling equipment with an attractive housing which appears to be nothing more than a sign, the public and/or employees would not normally be aware that the air is being sampled. Further, the positioning of the cassettes within the sampler deters people from touching the cassettes or otherwise interfering with the operation of the same.

Thus it can be seen that the sampler of this invention accomplishes at least all of its stated objectives.

I claim:

1. An air sampler comprising, a horizontally disposed, substantially block shaped upper housing portion having a front, a back, an upper end and a lower end, a horizontally disposed, substantially block shaped lower housing portion having a front, a back, an upper end and a lower end, a vertically disposed connecting housing portion extending between said upper and lower housing portions at the backs thereof, said connecting housing portion having a front portion for displaying a sign thereon, at least one air sampling cassette holder means positioned in said upper housing portion in a recessed manner in the said lower end thereof, an air sampling cassette positioned in said holder means so as to be substantially hidden from view when observing the same from either the front or sides thereof, at least one air pump means in said lower housing portion for drawing air into said air sampling cassette, and hose means interconnecting said air pump means and said holder means, said hose means extending through said connecting housing portion.

2. The apparatus of claim 1 wherein a light means is provided in said upper housing portion for illuminating the front portion of said connecting housing member.

3. The apparatus of claim 1 wherein a second air sampling cassette holder means is positioned in said upper housing portion and wherein a second air pump means is mounted in said lower housing portion.

* * * * *